United States Patent
Mercenier et al.

(10) Patent No.: US 8,603,492 B2
(45) Date of Patent: Dec. 10, 2013

(54) COMPLETE LIQUID NUTRITION FOR CHILDREN AT THE AGE OF 1-10 YEARS COMPRISING PROBIOTICS

(75) Inventors: Annick Mercenier, Bussigny (CH); Sophie Nutten, Lausanne (CH); Guenolee Prioult, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/319,961

(22) PCT Filed: May 11, 2010

(86) PCT No.: PCT/EP2010/056410
§ 371 (c)(1), (2), (4) Date: Jan. 12, 2012

(87) PCT Pub. No.: WO2010/130710
PCT Pub. Date: Nov. 18, 2010

(65) Prior Publication Data
US 2012/0121652 A1 May 17, 2012

(30) Foreign Application Priority Data

May 11, 2009 (EP) .................................. 09159925
May 11, 2009 (EP) .................................. 09159929

(51) Int. Cl.
*A61K 35/74* (2006.01)

(52) U.S. Cl.
USPC ...................................... 424/282.1; 424/93.4

(58) Field of Classification Search
None
See application file for complete search history.

(56) References Cited

U.S. PATENT DOCUMENTS

| 6,200,950 | B1 | 3/2001 | Mark et al. | |
| 2008/0206212 | A1* | 8/2008 | McMahon et al. | 424/93.45 |
| 2010/0074870 | A1* | 3/2010 | Russell et al. | 424/93.4 |

FOREIGN PATENT DOCUMENTS

| EP | 1227152 | 7/2002 |
| WO | WO 2004069156 | 8/2004 |
| WO | WO 2007093619 | 8/2007 |
| WO | WO 2008001086 | 1/2008 |
| WO | WO 2008106373 | 9/2008 |
| WO | WO 2008153377 | 12/2008 |

OTHER PUBLICATIONS

A. Taylor, et al., "Effects of probiotic supplementation for the first 6 months of life on allergen- and vaccine-specific immune responses," Clinical and Experimental Allergy, vol. 36, 2006, pp. 1227-1235.
R. Kekkonen, et al., "Probiotic Leuconostoc mesenteroids ssp. cremoris and *Streptococcus thermophilus* induce IL-12 and IFN-y production," World J. Gastroenterology, vol. 14, No. 8, Feb. 2008, pp. 1192-1203.
B. Foligne, et al., "Correlation between in vitro and in vivo immunomodulatory properties of lactid acid bacteria," World J. Gasternotoloyy, vol. 13, No. 2, Jan. 2007, pp. 236-243.
E. Brandt, et al., "Mast cells are required for experimental oral allergen-induced diarrhea," The Journal of Clinical Investigation, vol. 112, No. 11, Dec. 2003, pp. 1666-1677.
M. Schultz, et al., "Immunomodulatory consequences of oral administration of *Lactobacillus rhamnosus* strain GG in healthy volunteers," Journal of Dairy Research, vol. 70, 2003, pp. 165-173.
S. Salminen, et al., "Probiotics: how should they be defined?" Trends in Food Science and Technology, vol. 10, 1999, pp. 107-110.
D. Rachmilewitz, et al., "Toll-Like Receptor 9 Signaling Mediates the Anti-inflammatory Effects of Probiotics in Murine Experimental Colitis," Gastroenterology, vol. 126, 2004, pp. 520-528.
I. Castagliuolo, et al., "Beneficial effect of auto-aggregating *Lactobacillus crispatus* on experimentally induced colitis in mice," FEMS Immunology and Medical Microbiology, vol. 43, 2005, pp. 197-204.
S. Gill, et al., "Viability and dose-response studies on the effects of the immunoenhancing lactic acid bacterium *Lactobacillus rhamnosus* in mice," British Journal of Nutrition, vol. 86, 2001, pp. 285-289.
M. Kaila, et al., "Viabile versus inactivated *lactobacillus* strain GG in acute rotavirus diarrhoea," Archives of Disease in Childhood, vol. 72, 2005, pp. 51-53.
Search Report for International Application No. PCT/EP2010/056410 mailed Sep. 28, 2010.
Written Opinion for International Application No. PCT/EP2010/056410 mailed Sep. 28, 2010.

\* cited by examiner

*Primary Examiner* — Padma V Baskar
(74) *Attorney, Agent, or Firm* — K&L Gates LLP

(57) ABSTRACT

The present invention relates to the field of nutrition for children. In particular, the present invention relates to the nutritional compositions intended for children with an impaired function of the gastro-intestinal tract. One embodiment of the present invention relates to a nutritional composition to be administered to children with an impaired function of the gastrointestinal tract comprising probiotic micro-organisms. The probiotic micro-organisms may be non-replicating, for example bioactive heat treated probiotic micro-organisms.

9 Claims, 12 Drawing Sheets

COMPLETE LIQUID NUTRITION FOR CHILDREN AT THE AGE OF 1-10 YEARS COMPRISING PROBIOTICS

CROSS REFERENCE TO RELATED APPLICATIONS

The present application is a National Stage of International Application No. PCT/EP2010/056410, filed on May 11, 2010, which claims priority to European Patent Application No. 09159925.8, filed on May 11, 2009 and European Patent Application No. 09159929.0, filed on May 11, 2009, the entire contents of which are being incorporated herein by reference.

The present invention relates to the field of nutrition for children. In particular, the present invention relates to the nutritional compositions intended for children with an impaired function of the gastro-intestinal tract. One embodiment of the present invention relates to a nutritional composition to be administered to children with an impaired function of the gastrointestinal tract comprising probiotic micro-organisms. The probiotic micro-organisms may be non-replicating, for example bioactive heat treated probiotic micro-organisms.

Children have special nutritional needs. These needs vary greatly with the age and the developmental status of the child. Childhood is commonly understood as the time period between the stages of birth and puberty.

The significant changes the bodies of children undergo when they develop require a constant supply of nutrients to support this process. A balanced diet is best to provide children with all they need.

However, some children suffer from an impaired function of the gastrointestinal (GI) tract. As a consequence, such children are not always able to supply their body with sufficient amounts of nutrients.

Such children may suffer from reduced appetite, volume intolerance, constipation or diarrhea, for example, which either do not allow sufficient food intake or do not allow that the required nutrients are properly absorbed from the ingested food.

Specialized nutritional compositions have been developed for such cases so that the special requirements of children can still be met, even under unfavorable circumstances.

Typically, in cases of insufficient food intake the macronutrients in the food compositions are processed to make them easier to absorb.

It would nevertheless be desirable to also support the gut function, so that the digestive system works more effectively.

Children are often in close contact with many other children and require hence a strong immune system. Yet, depending on the developmental status, their immune system may still be immature. Malnutrition due to an impaired GI-tract function further weakens the immune system.

It would also be desirable if the composition had an anti-inflammatory effect.

Consequently, it would be desirable to provide children not only with nutritional support but also with support for the immune system, with a natural composition that allows to decrease the degree of inflammation in case a child is ill or recovering from illness and/or with means that allow a better functioning of the gut.

Hence, there is a need in the art for a nutritional composition that allows to provide children with specialized nutrition according to their specific needs while decreasing inflammation, boosting the immune system and/or improving digestion. It would be preferred if this was achieved by using natural ingredients that are safe to administer without side effects and that are easy to incorporate into nutritional supplements using industrial processing.

The present inventors have addressed this need. It was hence the objective of the present invention to improve the state of the art and to provide an nutritional composition to be administered to children that satisfies the needs expressed above.

The present inventors were surprised that they could achieve this object by the subject matter of the independent claim. The dependant claims further develop the idea of the present invention.

Accordingly, the present inventors propose to provide specific oral nutritional compositions to be administered to children suffering from an impaired function of the GI-tract comprising probiotics.

Children are to be understood for the purpose of the present invention as humans between 1 and 13 years old.

Probiotics were found to be able to provide their health benefits in the framework of liquid nutritional compositions.

As liquid nutritional compositions to be administered to specific patients usually have a shelf life that exceeds the shelf life of yoghurt drinks comprising probiotics, probiotics were usually not added to such nutritional compositions, because of uncertainties that the viability of the probiotics can be ensured during an extended shelf life.

The present inventors were now able to show that even non-replicating probiotics can provide the health benefits of probiotics and may even have improved benefits.

Hence one embodiment of the present invention is a composition to be administered to children that provides complete nutrition to a patient and comprises probiotic micro-organisms.

The children may suffer from an impaired gastro-intestinal tract function, for example.

A composition provides complete nutrition if a patient obtains all required nutrients from this composition and no additional food sources are required.

The composition of the present invention may be provided as nutritional composition to be administered orally or as a nutritional composition to be administered enterally via tube feeding.

The nutritional composition of the present invention provides a balanced peptide profile to support nitrogen absorption and growth. The peptides may be completely or partially whey-based to facilitate gastric emptying.

As a completely whey based protein source enzymatically hydrolyzed whey protein may be used.

Alternatively, a mixture of milk protein concentrate and whey protein concentrate may be use in a ratio of approximately 1:1.

The nutritional composition of the present invention may be to be administered to children at an age of 1 to 10 years.

One embodiment of the present invention is a composition having a caloric density in the range of 0.9-1.1 kcal/ml, an osmolality in the range of 250-270 mOsm/kg water, and comprising a protein source accounting for about 11-13% of the calories of the composition, a carbohydrate source accounting for about 43-56% of the calories of the composition, and a lipid source accounting for about 32-45% of the calories of the composition.

High MCT:LCT ratios may be chosen to decrease the potential for fat malabsorption.

Hence, the MCT (medium chain triglycerides):LCT (long chain triglycerides) ratio may be in the range of 20:80 to 24:76 for normal patients. For patients suffering from fat malabsorption it may be preferred to employ an MCT:LCT ratio of around 58:42 to 62:38.

The composition of the present invention may contain fibres to help promote a healthy gut microbiota. A mixture of pea fibre, oligofructose, and inulin may be used. The fibres may be present in an amount of 5.5 to 7.5 g/L.

The composition of the present invention may have an NPC:N ratio in the range of 175:1 to 190:1. The nonprotein kcalorie to nitrogen ratio (NPC:N) is calculated by calculating the grams of nitrogen supplied per day (1 g N=6.25 g protein) and by dividing the total nonprotein kcalories by grams of nitrogen Typically, nutritional supplements with a NPC:N Ratio in the range of 80:1 is used for the most severely stressed patients, a NPC:N Ratio in the range of 100:1 is used for severely stressed patients and a NPC:N Ratio in the range of 150:1 is used for unstressed patients.

For children too high protein contents are usually not needed. However, in case of severely stressed children the NPC:N ratio may be adjusted accordingly.

The compositions of the present invention may have a lipid source with a n6:n3 fatty acid ratio in the range of 4.5:1 to 5.5:1.

Typically, the composition of the present invention comprises about 83-87% free water. Free water is essential to meet minimum fluid requirements. Typically, patients with an impaired GI function do not drink enough.

The compositions of the present invention may be used for the nutritional management of Bowel Resections, Cystic Fibrosis, Cerebral Palsy, Oncology, Pancreatitis, HIV/AIDS, Malabsorption, Short-Bowel Syndrome, Developmental Delay, Malnutrition, IBD (Inflammatory Bowel Disease), Fat Malabsorption, Constipation, Crohn's Disease, Diarrhea, Gastrointestinal Impairment, Gluten Intolerance, Impaired Digestion and Absorption, Lactose Intolerance, Limited Gut Function, Pediatric Gastrointestinal Disorders, Special Pediatric Nutritional Needs, and/or Failure to Thrive.

The composition may comprise in part or only non-replicating probiotic micro-organisms.

The inventors were surprised to see that, e.g., in terms of an immune boosting effect and/or in terms of an anti-inflammatory effect non-replicating probiotic microorganisms may even be more effective than replicating probiotic microorganisms.

This is surprising since probiotics are often defined as "live micro-organisms that when administered in adequate amounts confer health benefits to the host" (FAO/WHO Guidelines). The vast majority of published literature deals with live probiotics. In addition, several studies investigated the health benefits delivered by non-replicating bacteria and most of them indicated that inactivation of probiotics, e.g. by heat treatment, leads to a loss of their purported health benefit (Rachmilewitz, D., et al., 2004, Gastroenterology 126:520-528; Castagliuolo, et al., 2005, FEMS Immunol. Med. Microbiol. 43:197-204; Gill, H. S. and K. J. Rutherfurd, 2001, Br.J.Nutr. 86:285-289; Kaila, M., et al., 1995, Arch. Dis. Child 72:51-53.). Some studies showed that killed probiotics may retain some health effects (Rachmilewitz, D., et al., 2004, Gastroenterology 126:520-528; Gill, H. S. and K. J. Rutherfurd, 2001,Br. J. Nutr. 86:285-289), but clearly, living probiotics were regarded in the art so far as more performing.

The composition according to the present invention may comprise probiotic micro-organisms in any effective amount, for example in an amount corresponding to about $10^6$ to $10^{12}$ cfu/g dry weight.

The probiotic micro-organisms may be non-replicating probiotic micro-organisms.

"Non-replicating" probiotic micro-organisms include probiotic bacteria which have been heat treated. This includes micro-organisms that are inactivated, dead, non-viable and/or present as fragments such as DNA, metabolites, cytoplasmic compounds, and/or cell wall materials.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h).

Probiotics are defined for the purpose of the present invention as "Microbial cell preparations or components of microbial cells with a beneficial effect on the health or well-being of the host." (Salminen S, Ouwehand A. Benno Y. et al "Probiotics: how should they be defined" Trends Food Sci. Technol. 1999:10 107-10).

The possibility to use non-replicating probiotic micro-organisms offers several advantages. In severely immuno-compromised patients, the use of live probiotics may be limited in exceptional cases due to a potential risk to develop bacteremia. Non-replicating probiotics may be used without any problem.

Additionally, the provision of non-replicating probiotic micro-organisms allows the hot reconstitution while retaining health benefit.

The compositions of the present invention comprise probiotic micro-organisms and/or non-replicating probiotic micro-organisms in an amount sufficient to at least partially produce a health benefit. An amount adequate to accomplish this is defined as "a therapeutically effective dose". Amounts effective for this purpose will depend on a number of factors known to those of skill in the art such as the weight and general health state of the patient, and on the effect of the food matrix.

In prophylactic applications, compositions according to the invention are administered to a consumer susceptible to or otherwise at risk of a disorder in an amount that is sufficient to at least partially reduce the risk of developing that disorder. Such an amount is defined to be "a prophylactic effective dose". Again, the precise amounts depend on a number of factors such as the patient's state of health and weight, and on the effect of the food matrix.

Those skilled in the art will be able to adjust the therapeutically effective dose and/or the prophylactic effective dose appropriately.

In general the composition of the present invention contains probiotic micro-organisms and/or non-replicating probiotic micro-organisms in a therapeutically effective dose and/or in a prophylactic effective dose.

Typically, the therapeutically effective dose and/or the prophylactic effective dose is in the range of about 0.005 mg-1000 mg probiotic micro-organisms and/or non-replicating, probiotic micro-organisms per daily dose.

In terms of numerical amounts, the "short-time high temperature" treated non-replicating micro-organisms may be present in the composition in an amount corresponding to between $10^4$ and $10^{12}$ equivalent cfu/g of the dry composition. Obviously, non-replicating micro-organisms do not form colonies, consequently, this term is to be understood as the amount of non replicating micro-organisms that is obtained from $10^4$ and $10^{12}$ cfu/g replicating bacteria. This includes micro-organisms that are inactivated, non-viable or dead or present as fragments such as DNA or cell wall or cytoplasmic compounds. In other words, the quantity of micro-organisms which the composition contains is expressed in terms of the colony forming ability (cfu) of that quantity of micro-organisms as if all the micro-organisms were alive irrespective of whether they are, in fact, non replicating, such as inactivated or dead, fragmented or a mixture of any or all of these states.

Preferably the non-replicating micro-organisms are present in an amount equivalent to between $10^4$ to $10^9$ cfu/g of dry composition, even more preferably in an amount equivalent to between $10^5$ and $10^9$ cfu/g of dry composition.

The probiotics may be rendered non-replicating by any method that is known in the art.

The technologies available today to render probiotic strains non-replicating are usually heat-treatment, γ-irradiation, UV light or the use of chemical agents (formalin, paraformaldehyde).

It would be preferred to use a technique to render probiotics non-replicating that is relatively easy to apply under industrial circumstances in the food industry.

Most products on the market today that contain probiotics are heat treated during their production. It would hence be convenient, to be able to heat treat probiotics either together with the produced product or at least in a similar way, while the probiotics retain or improve their beneficial properties or even gain a new beneficial property for the consumer.

However, inactivation of probiotic micro-organisms by heat treatments is associated in the literature generally with an at least partial loss of probiotic activity.

The present inventors have now surprisingly found, that rendering probiotic micro-organisms non-replicating, e.g., by heat treatment, does not result in the loss of probiotic health benefits, but—to the contrary—may enhance existing health benefits and even generate new health benefits.

Hence, one embodiment of the present invention is a composition wherein the non-replicating probiotic micro-organisms were rendered non-replicating by a heat-treatment.

Such a heat treatment may be carried out at at least 71.5° C. for at least 1 second.

Long-term heat treatments or short-term heat treatments may be used.

In industrial scales today usually short term heat treatments, such as UHT-like heat treatments are preferred. This kind of heat treatment reduces bacterial loads, and reduces the processing time, thereby reducing the spoiling of nutrients.

The inventors demonstrate for the first time that probiotics micro-organisms, heat treated at high temperatures for short times exhibit anti-inflammatory immune profiles regardless of their initial properties. In particular either a new anti-inflammatory profile is developed or an existing anti-inflammatory profile is enhanced by this heat treatment.

It is therefore now possible to generate non replicating probiotic micro-organisms with anti-inflammatory immune profiles by using specific heat treatment parameters that correspond to typical industrially applicable heat treatments, even if live counterparts are not anti-inflammatory strains.

Hence, for example, the heat treatment may be a high temperature treatment at about 71.5-150° C. for about 1-120 seconds. The high temperature treatment may be a high temperature/short time (HTST) treatment or a ultra-high temperature (UHT) treatment.

The probiotic micro-organisms may be subjected to a high temperature treatment at about 71.5-150° C. for a short term of about 1-120 seconds.

More preferred the micro-organisms may be subjected to a high temperature treatment at about 90-140° C., for example 90°-120° C., for a short term of about 1-30 seconds.

This high temperature treatment renders the micro-organisms at least in part non-replicating.

The high temperature treatment may be carried out at normal atmospheric pressure but may be also carried out under high pressure. Typical pressure ranges are form 1 to 50 bar, preferably from 1-10 bar, even more preferred from 2 to 5 bar. Obviously, it is preferred if the probiotics are heat treated in a medium that is either liquid or solid, when the heat is applied. An ideal pressure to be applied will therefore depend on the nature of the composition which the micro-organisms are provided in and on the temperature used.

The high temperature treatment may be carried out in the temperature range of about 71.5-150° C., preferably of about 90-120° C., even more preferred of about 120-140° C.

The high temperature treatment may be carried out for a short term of about 1-120 seconds, preferably, of about 1-30 seconds, even more preferred for about 5-15 seconds.

This given time frame refers to the time the probiotic micro-organisms are subjected to the given temperature. Note, that depending on the nature and amount of the composition the micro-organisms are provided in and depending on the architecture of the heating apparatus used, the time of heat application may differ.

Typically, however, the composition of the present invention and/or the micro-organisms are treated by a high temperature short time (HTST) treatment, flash pasteurization or a ultra high temperature (UHT) treatment.

A UHT treatment is Ultra-high temperature processing or a ultra-heat treatment (both abbreviated UHT) involving the at least partial sterilization of a composition by heating it for a short time, around 1-10 seconds, at a temperature exceeding 135° C. (275° F.), which is the temperature required to kill bacterial spores in milk. For example, processing milk in this way using temperatures exceeding 135° C. permits a decrease of bacterial load in the necessary holding time (to 2-5 s) enabling a continuous flow operation.

There are two main types of UHT systems: the direct and indirect systems. In the direct system, products are treated by steam injection or steam infusion, whereas in the indirect system, products are heat treated using plate heat exchanger, tubular heat exchanger or scraped surface heat exchanger. Combinations of UHT systems may be applied at any step or at multiple steps in the process of product preparation.

A HTST treatment is defined as follows (High Temperature/Short Time): Pasteurization method designed to achieve a 5-log reduction, killing 99.9999% of the number of viable micro-organisms in milk. This is considered adequate for destroying almost all yeasts, molds and common spoilage bacteria and also ensure adequate destruction of common pathogenic heat resistant organisms. In the HTST process milk is heated to 71.7° C. (161° F.) for 15-20 seconds.

Flash pasteurization is a method of heat pasteurization of perishable beverages like fruit and vegetable juices, beer and dairy products. It is done prior to filling into containers in order to kill spoilage micro-organisms, to make the products safer and extend their shelf life. The liquid moves in controlled continuous flow while subjected to temperatures of 71.5° C. (160° F.) to 74° C. (165° F.) for about 15 to 30 seconds.

For the purpose of the present invention the term "short time high temperature treatment" shall include high-temperature short time (HTST) treatments, UHT treatments, and flash pasteurization, for example.

Since such a heat treatment provides non-replicating probiotics with an improved anti-inflammatory profile, the composition of the present invention may be for use in the prevention or treatment of inflammatory disorders.

The inflammatory disorders that can be treated or prevented by the composition of the present invention are not particularly limited. For example, they may be selected from the group consisting of acute inflammations such as sepsis; burns; and chronic inflammation, such as inflammatory bowel disease, e.g., Crohn's disease, ulcerative colitis, pouchitis; necrotizing enterocolitis; skin inflammation, such as UV or chemical-induced skin inflammation, eczema, reactive skin; irritable bowel syndrome; eye inflammation; allergy, asthma; and combinations thereof.

If long term heat treatments are used to render the probiotic micro-organisms non-replicating, such a heat treatment may be carried out in the temperature range of about 70-150° C. for about 3 minutes—2 hours, preferably in the range of 80-140° C. from 5 minutes—40 minutes.

While the prior art generally teaches that bacteria rendered non-replicating by long-term heat-treatments are usually less efficient than live cells in terms of exerting their probiotic properties, the present inventors were able to demonstrate that heat-treated probiotics are superior in stimulating the immune system compared to their live counterparts.

The present invention relates also to an composition comprising probiotic micro-organisms that were rendered non-replicating by a heat treatment at at least about 70° C. for at least about 3 minutes.

The immune boosting effects of non-replicating probiotics were confirmed by in vitro immunoprofiling. The in vitro model used uses cytokine profiling from human Peripheral Blood Mononuclear Cells (PBMCs) and is well accepted in the art as standard model for tests of immunomodulating compounds (Schultz et al., 2003, Journal of Dairy Research 70, 165-173; Taylor et al., 2006, Clinical and Experimental Allergy, 36, 1227-1235; Kekkonen et al., 2008, World Journal of Gastroenterology, 14, 1192-1203)

The in vitro PBMC assay has been used by several authors/research teams for example to classify probiotics according to their immune profile, i.e. their anti- or pro-inflammatory characteristics (Kekkonen et al., 2008, World Journal of Gastroenterology, 14, 1192-1203). For example, this assay has been shown to allow prediction of an anti-inflammatory effect of probiotic candidates in mouse models of intestinal colitis (Foligne, B., et al., 2007, World J. Gastroenterol. 13:236-243). Moreover, this assay is regularly used as read-out in clinical trials and was shown to lead to results coherent with the clinical outcomes (Schultz et al., 2003, Journal of Dairy Research 70, 165-173; Taylor et al., 2006, Clinical and Experimental Allergy, 36, 1227-1235).

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, allergy can be mitigated, down-regulated or prevented by restoring an appropriate balance between the Th1 and Th2 arms of the immune system. This implies the necessity to reduce the Th2 responses or to enhance, at least transiently, the Th1 responses. The latter would be characteristic of an immune boost response, often accompanied by for example higher levels of IFNγ, TNF-α and IL-12. (Kekkonen et al., 2008, World Journal of Gastroenterology, 14, 1192-1203; Viljanen M. et al., 2005, Allergy, 60, 494-500)

The composition of the present invention allows it hence to treat or prevent disorders that are related to a compromised immune defence.

Consequently, the disorders linked to a compromised immune defence that can be treated or prevented by the composition of the present invention are not particularly limited.

For example, they may be selected from the group consisting of infections, in particular bacterial, viral, fungal and/or parasite infections; phagocyte deficiencies; low to severe immunodepression levels such as those induced by stress or immunodepressive drugs, chemotherapy or radiotherapy; natural states of less immunocompetent immune systems such as those of the neonates; allergies; and combinations thereof.

The composition described in the present invention allows it also to enhance a patient's response to vaccines, in particular to oral vaccines.

Any amount of non-replicating micro-organisms will be effective. However, it is generally preferred, if at least 90%, preferably, at least 95%, more preferably at least 98%, most preferably at least 99%, ideally at least 99.9%, most ideally all of the probiotics are non-replicating.

In one embodiment of the present invention all micro-organisms are non-replicating.

Consequently, in the composition of the present invention at least 90%, preferably, at least 95%, more preferably at least 98%, most preferably at least 99%, ideally at least 99.9%, most ideally all of the probiotics may be non-replicating.

All probiotic micro-organisms may be used for the purpose of the present invention.

For example, the probiotic micro-organisms may be selected from the group consisting of bifidobacteria, lactobacilli, propionibacteria, or combinations thereof, for example *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli* and/or mixtures thereof.

The composition in accordance with the present invention may, for example comprise probiotic micro-organisms selected from the group consisting of *Bifidobacterium longum* NCC 3001, *Bifidobacterium longum* NCC 2705, *Bifidobacterium breve* NCC 2950, *Bifidobacterium lactis* NCC 2818, *Lactobacillus johnsonii* La1, *Lactobacillus paracasei* NCC 2461, *Lactobacillus rhamnosus* NCC 4007, *Lactobacillus reuteri* DSM17983, *Lactobacillus reuteri* ATCC55730, *Streptococcus thermophilus* NCC 2019, *Streptococcus thermophilus* NCC 2059, *Lactobacillus casei* NCC 4006, *Lactobacillus acidophilus* NCC 3009, *Lactobacillus casei* ACA-DC 6002 (NCC 1825), *Escherichia coli* Nissle, *Lactobacillus bulgaricus* NCC 15, *Lactococcus lactis* NCC 2287, or combinations thereof.

All these strains were either deposited under the Budapest treaty and/or are commercially available.

The strains have been deposited under the Budapest treaty as follows:
*Bifidobacterium longum* NCC 3001: ATCC BAA-999
*Bifidobacterium longum* NCC 2705: CNCM I-2618
*Bifidobacterium breve* NCC 2950 CNCM I-3865
*Bifidobacterium lactis* NCC 2818: CNCM I-3446
*Lactobacillus paracasei* NCC 2461: CNCM I-2116

*Lactobacillus rhamnosus* NCC 4007: CGMCC 1.3724
*Streptococcus themophilus* NCC 2019: CNCM I-1422
*Streptococcus themophilus* NCC 2059: CNCM I-4153
*Lactococcus lactis* NCC 2287: CNCM I-4154
*Lactobacillus casei* NCC 4006: CNCM I-1518
*Lactobacillus casei* NCC 1825: ACA-DC 6002
*Lactobacillus acidophilus* NCC 3009: ATCC 700396
*Lactobacillus bulgaricus* NCC 15: CNCM I-1198
*Lactobacillus johnsonii* La1 CNCM I-1225
*Lactobacillus reuteri* DSM17983 DSM17983
*Lactobacillus reuteri* ATCC55730 ATCC55730
*Escherichia coli* Nissle 1917: DSM 6601

Those skilled in the art will understand that they can freely combine all features of the present invention described herein, without departing from the scope of the invention as disclosed.

Further advantages and features of the present invention are apparent from the following Examples and Figures.

FIGS. 1A and B show the enhancement of the anti-inflammatory immune profiles of probiotics treated with "short-time high temperatures".

FIG. 2 shows non anti-inflammatory probiotic strains that become anti-inflammatory, i.e. that exhibit pronounced anti-inflammatory immune profiles in vitro after being treated with "short-time high temperatures".

FIGS. 3A and B show probiotic strains in use in commercially available products that exhibit enhanced or new anti-inflammatory immune profiles in vitro after being treated with "short-time high temperatures".

FIGS. 4A and B show dairy starter strains (i.e. Lc1 starter strains) that exhibits enhanced or new anti-inflammatory immune profiles in vitro upon heat treatment at high temperatures.

FIG. 5 shows a non anti-inflammatory probiotic strain that exhibits anti-inflammatory immune profiles in vitro after being treated with HTST treatments.

FIG. 6: Principal Component Analysis on PBMC data (IL-12p40, IFN-γ, TNF-α, IL-10) generated with probiotic and dairy starter strains in their live and heat treated (140° C. for 15 second) forms. Each dot represents one strain either live or heat treated identified by its NCC number or name.

Figure 9:
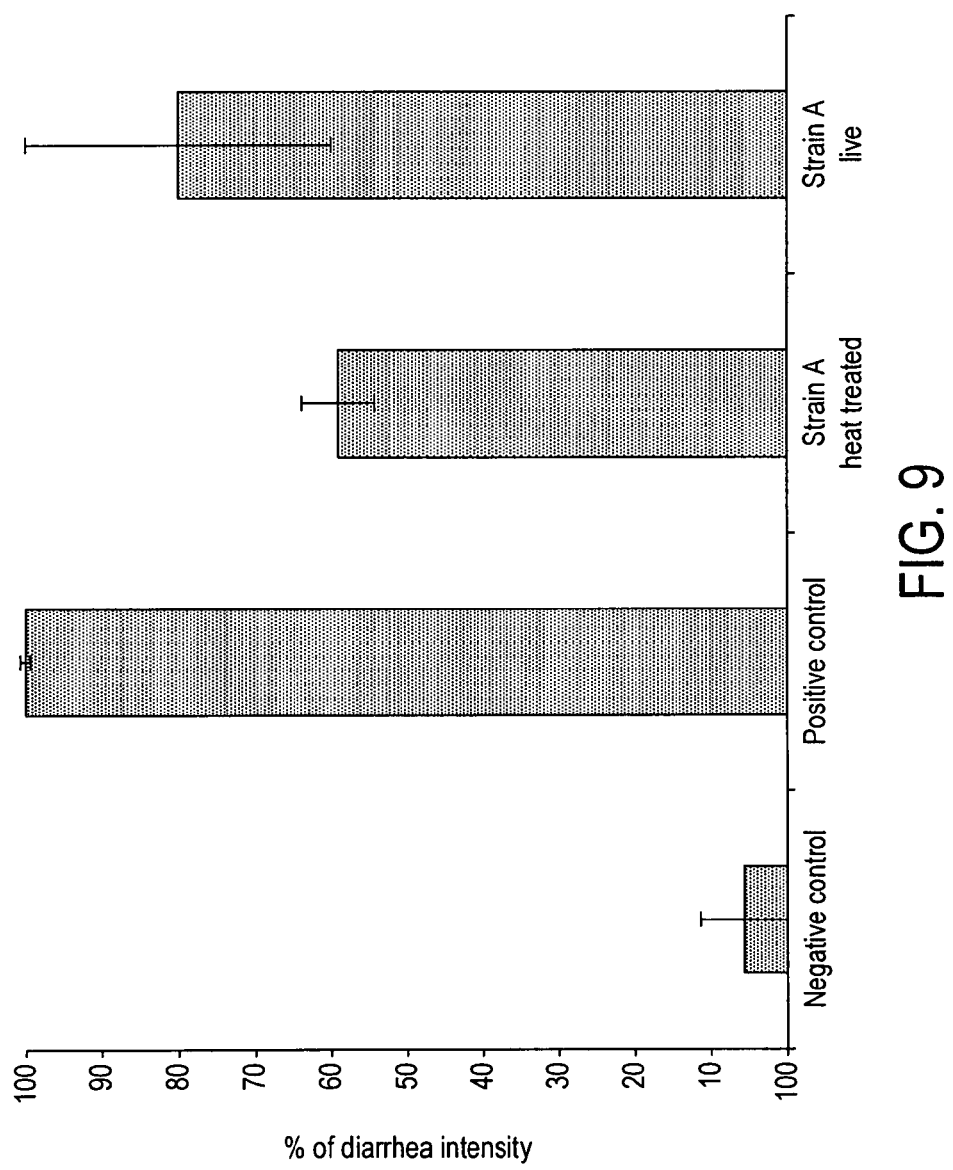

FIG. 9 shows the percentage of diarrhea intensity observed in OVA-sensitized mice challenged with saline (negative control), OVA-sensitized mice challenged with OVA (positive control) and OVA-sensitized mice challenged with OVA and treated with heat-treated or live *Bifidobacterium breve* NCC2950. Results are displayed as the percentage of diarrhea intensity (Mean±SEM calculated from 4 independent experiments) with 100% of diarrhea intensity corresponding to the symptoms developed in the positive control (sensitized and challenged by the allergen) group.

EXAMPLE 1

Methodology
Bacterial Preparations:

The health benefits delivered by live probiotics on the host immune system are generally considered to be strain specific. Probiotics inducing high levels of IL-10 and/or inducing low levels of pro-inflammatory cytokines in vitro (PBMC assay) have been shown to be potent anti-inflammatory strains in vivo (Foligné, B., et al., 2007, World J. Gastroenterol. 13:236-243).

Several probiotic strains were used to investigate the anti-inflammatory properties of heat treated probiotics. These were *Bifidobacterium longum* NCC 3001, *Bifidobacterium longum* NCC 2705, *Bifidobacterium breve* NCC 2950, *Bifidobacterium lactis* NCC 2818, *Lactobacillus paracasei* NCC 2461, *Lactobacillus rhamnosus* NCC 4007, *Lactobacillus casei* NCC 4006, *Lactobacillus acidophilus* NCC 3009, *Lactobacillus casei* ACA-DC 6002 (NCC 1825), and *Escherichia coli* Nissle. Several starter culture strains including some strains commercially used to produce Nestlé Lc1 fermented products were also tested: *Streptococcus thermophilus* NCC 2019, *Streptococcus thermophilus* NCC 2059, *Lactobacillus bulgaricus* NCC 15 and *Lactococcus lactis* NCC 2287.

Bacterial cells were cultivated in conditions optimized for each strain in 5-15 L bioreactors. All typical bacterial growth media are usable. Such media are known to those skilled in the art. When pH was adjusted to 5.5, 30% base solution (either NaOH or $Ca(OH)_2$) was added continuously. When adequate, anaerobic conditions were maintained by gassing headspace with $CO_2$. *E. coli* was cultivated under standard aerobic conditions.

Bacterial cells were collected by centrifugation (5,000×g, 4° C.) and re-suspended in phosphate buffer saline (PBS) in adequate volumes in order to reach a final concentration of around $10^9$-$10^{10}$ cfu/ml. Part of the preparation was frozen at −80° C. with 15% glycerol. Another part of the cells was heat treated by:

Ultra High Temperature: 140° C. for 15 sec; by indirect steam injection.
High Temperature Short Time (HTST): 74° C., 90° C. and 120° C. for 15 sec by indirect steam injection
Long Time Low Temperature (85° C., 20 min) in water bath
Upon heat treatment, samples were kept frozen at −80° C. until use.

In Vitro Immunoprofiling of Bacterial Preparations:

The immune profiles of live and heat treated bacterial preparations (i.e. the capacity to induce secretion of specific cytokines from human blood cells in vitro) were assessed. Human peripheral blood mononuclear cells (PBMCs) were isolated from blood filters. After separation by cell density gradient, mononuclear cells were collected and washed twice with Hank's balanced salt solution. Cells were then resuspended in Iscove's Modified Dulbecco's Medium (IMDM, Sigma) supplemented with 10% foetal calf serum (Bioconcept, Paris, France), 1% L-glutamine (Sigma), 1% penicillin/streptomycin (Sigma) and 0.1% gentamycin (Sigma). PBMCs ($7\times10^5$ cells/well) were then incubated with live and heat treated bacteria (equivalent $7\times10^6$ cfu/well) in 48 well plates for 36 h. The effects of live and heat treated bacteria were tested on PBMCs from 8 individual donors splitted into two separated experiments. After 36 h incubation, culture plates were frozen and kept at −20° C. until cytokine measurement. Cytokine profiling was performed in parallel (i.e. in the same experiment on the same batch of PBMCs) for live bacteria and their heat-treated counterparts.

Levels of cytokines (IFN-γ, IL-12p40, TNF-α and IL-10) in cell culture supernatants after 36 h incubation were determined by ELISA (R&D DuoSet Human IL-10, BD OptEIA Human IL12p40, BD OptEIA Human TNFα, BD OptEIA Human IFN-γ) following manufacturer's instructions. IFN-γ, IL-12p40 and TNF-α are pro-inflammatory cytokines, whereas IL-10 is a potent anti-inflammatory mediator. Results are expressed as means (pg/ml) +/− SEM of 4 individual donors and are representative of two individual experiments performed with 4 donors each. The ratio IL-12p40/IL-10 is calculated for each strain as a predictive value of in vivo anti-inflammatory effect (Foligné, B., et al., 2007, World J. Gastroenterol. 13:236-243).

Numerical cytokine values (pg/ml) determined by ELISA (see above) for each strain were transferred into BioNumerics v5.10 software (Applied Maths, Sint-Martens-Latem, Belgium). A Principal Component Analysis (PCA, dimensioning technique) was performed on this set of data. Subtraction of the averages over the characters and division by the variances over the characters were included in this analysis.

Results

Figure 4A:
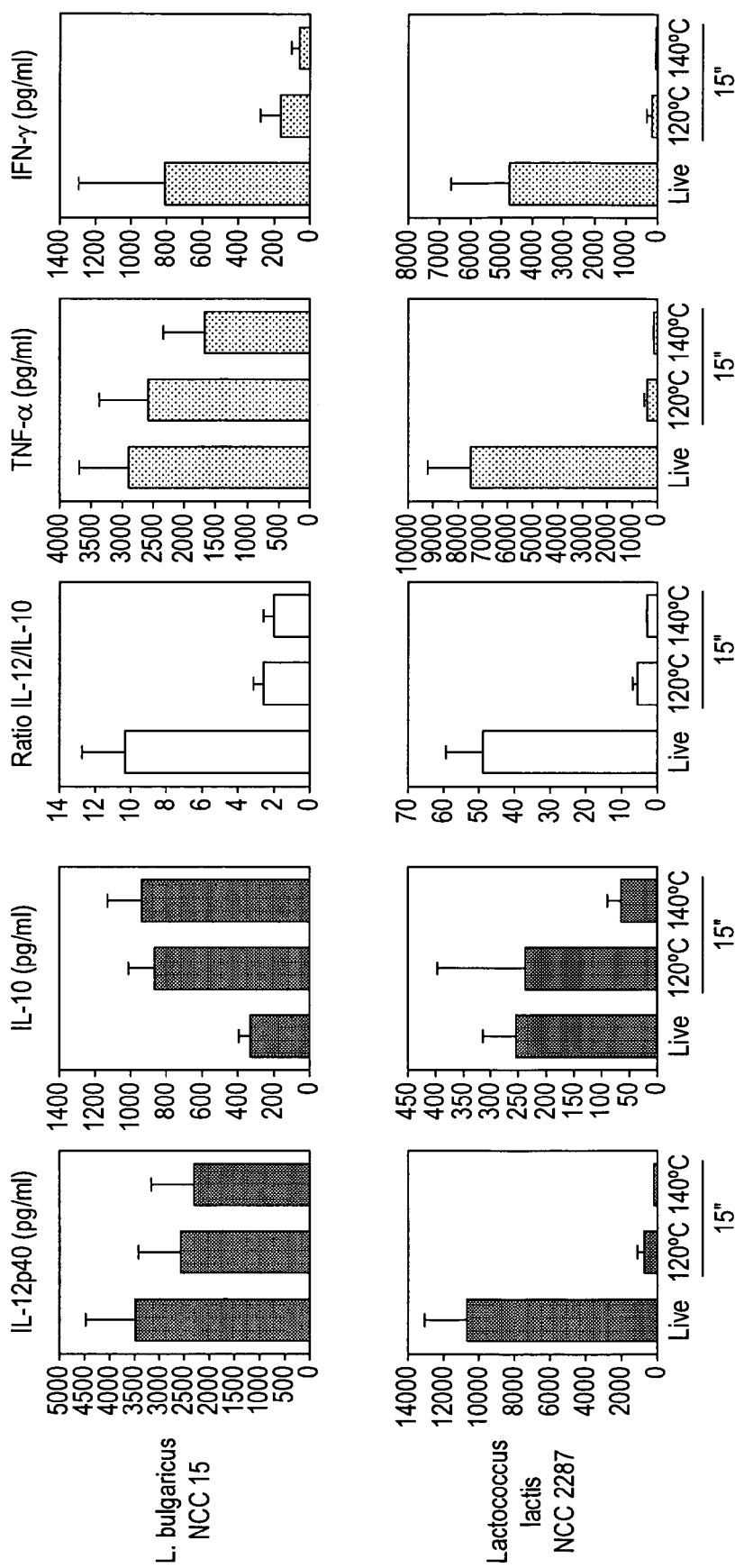
Figure 4B:
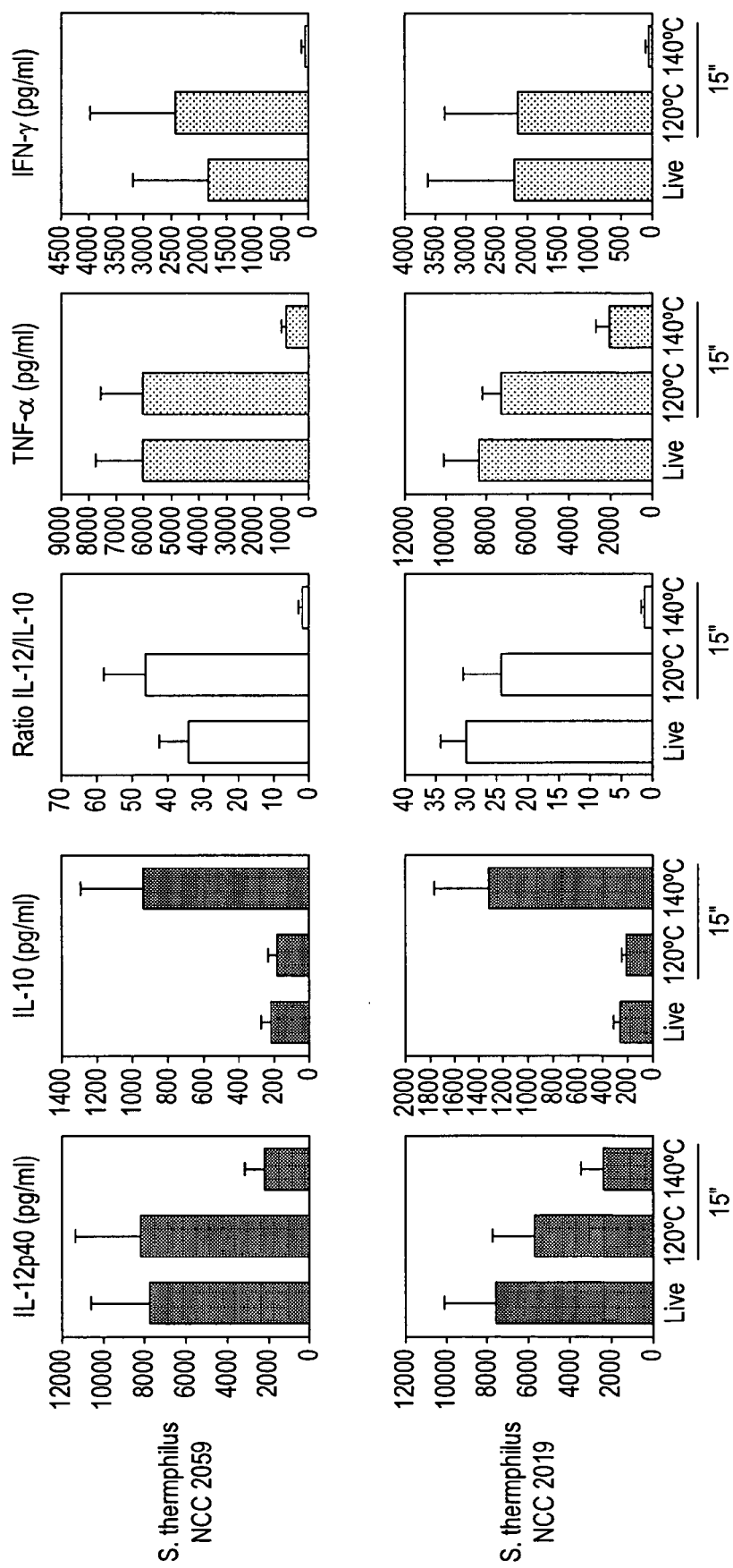
Figure 5:
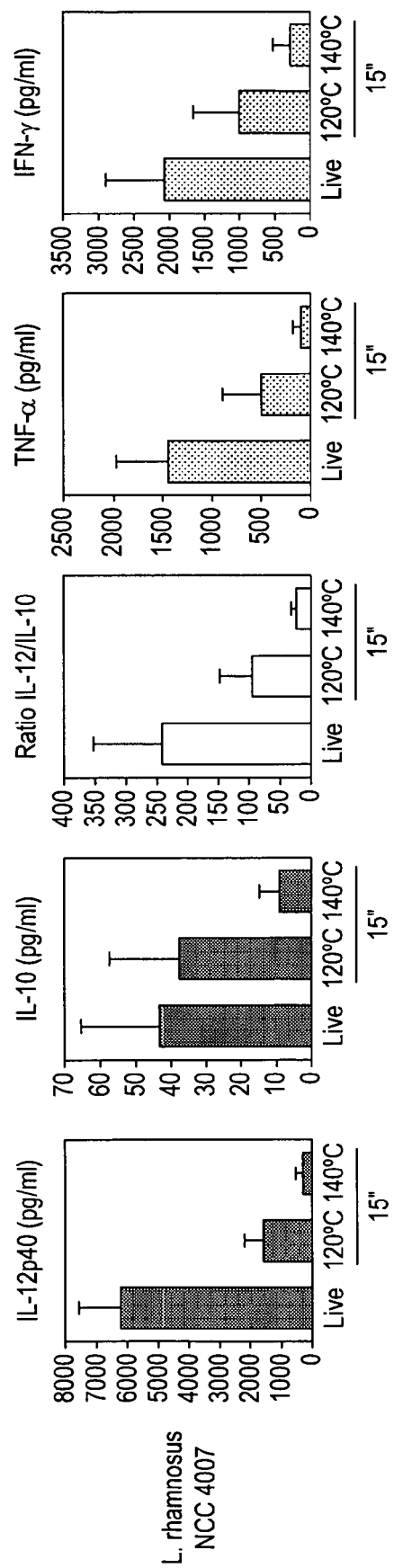
Figure 6:
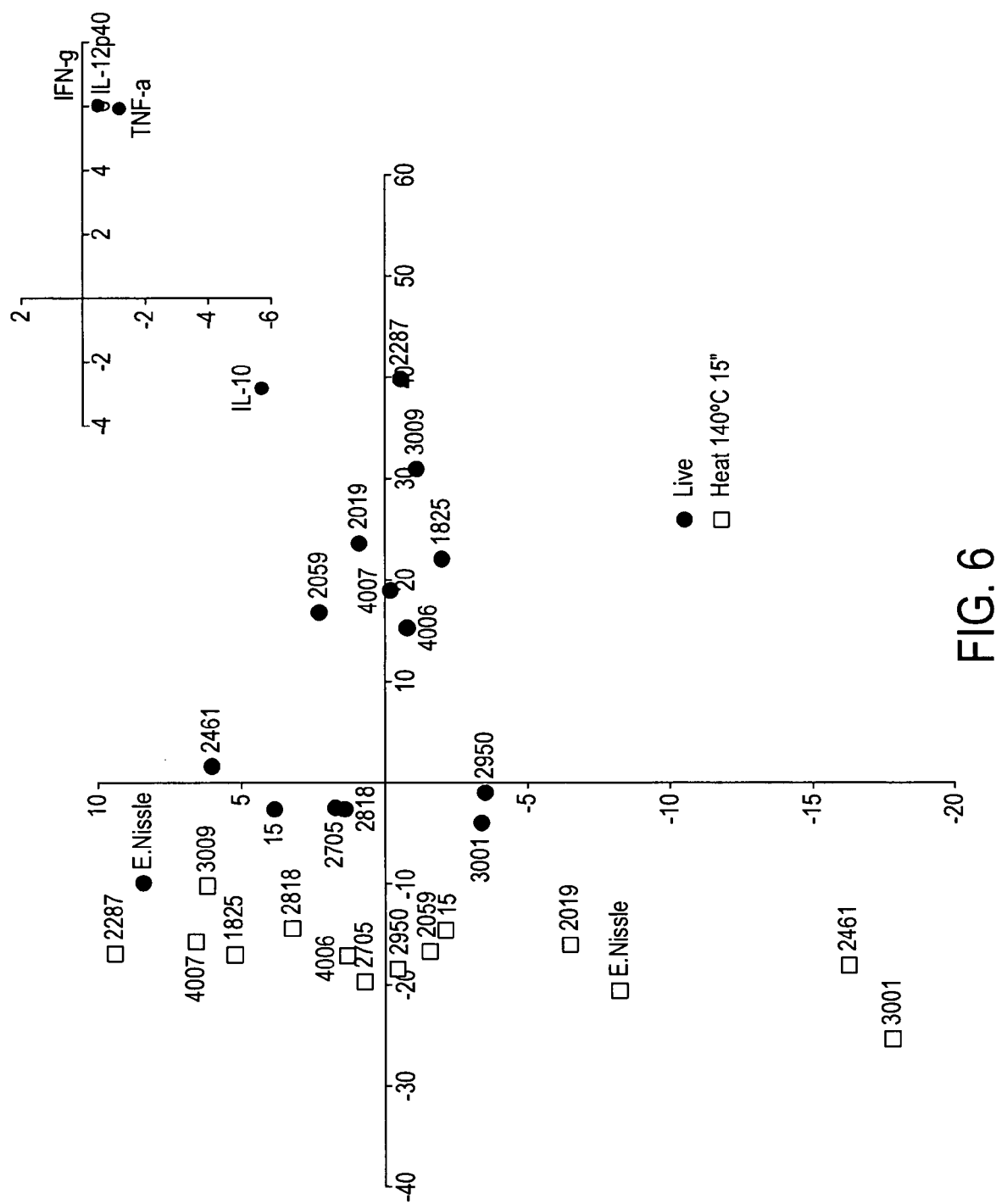
Figure 7:
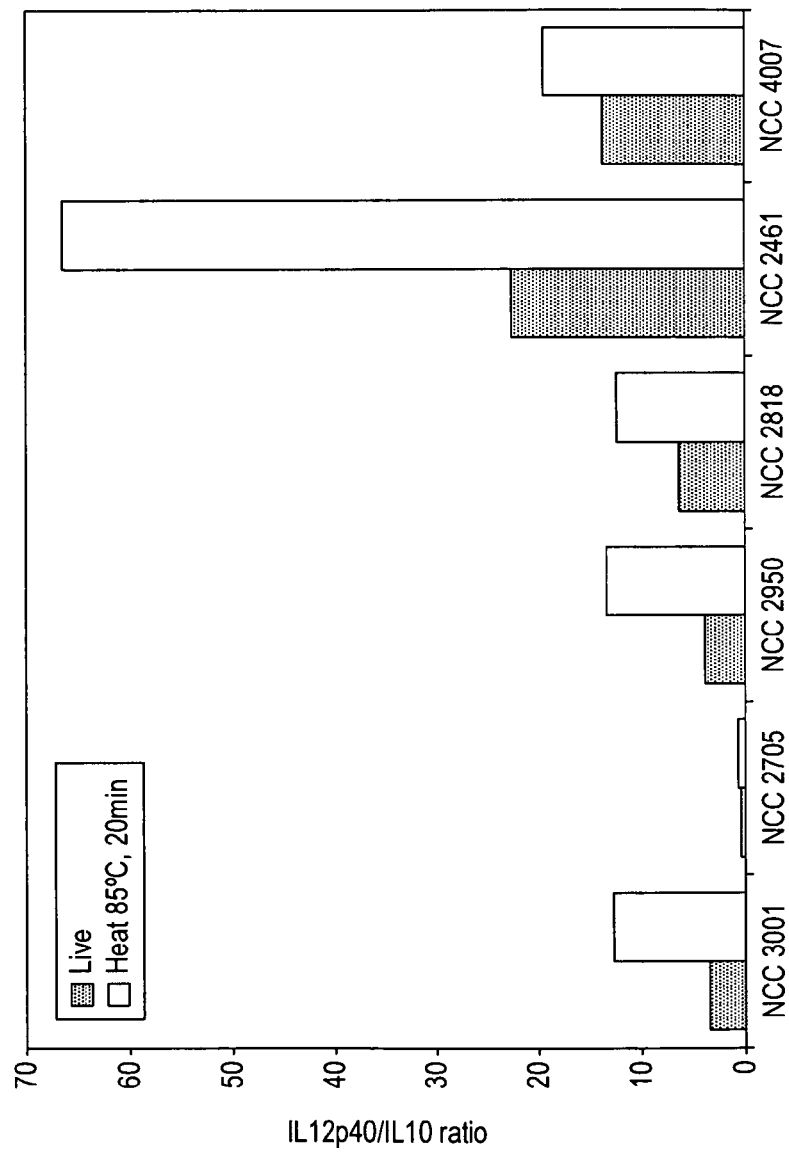
FIG. 7 shows IL-12p40/IL-10 ratios of live and heat treated (85° C., 20 min) strains. Overall, heat treatment at 85° C. for 20 min leads to an increase of IL-12p40/IL-10 ratios as opposed to "short-time high temperature" treatments of the present invention (FIGS. 1, 2, 3, 4 and 5).

Anti-inflammatory profiles generated by Ultra High Temperature (UHT)/High Temperature Short Time (HTST)-like treatments The probiotic strains under investigation were submitted to a series of heat treatments (Ultra High Temperature (UHT), High Temperature Short Time (HTST) and 85° C. for 20 min) and their immune profiles were compared to those of live cells in vitro. Live micro-organisms (probiotics and/or dairy starter cultures) induced different levels of cytokine production when incubated with human PBMC (FIGS. 1, 2, 3, 4 and 5). Heat treatment of these micro-organisms modified the levels of cytokines produced by PBMC in a temperature dependent manner. "Short-time high temperature" treatments (120° C. or 140° C. for 15") generated non replicating bacteria with anti-inflammatory immune profiles (FIGS. 1, 2, 3 and 4). Indeed, UHT-like treated strains (140° C., 15 sec) induced less pro-inflammatory cytokines (TNF-α, IFN-γ, IL-12p40) while maintaining or inducing additional IL-10 production (compared to live counterparts). The resulting IL-12p40/IL-10 ratios were lower for any UHT-like treated strains compared to live cells (FIGS. 1, 2, 3 and 4). This observation was also valid for bacteria treated by HTST-like treatments, i.e. submitted to 120° C. for 15 sec (FIGS. 1, 2, 3 and 4), or 74° C. and 90° C. for 15 sec (FIG. 5). Heat treatments (UHT-like or HTST-like treatments) had a similar effect on in vitro immune profiles of probiotic strains (FIGS. 1, 2, 3 and 5) and dairy starter cultures (FIG. 4). Principal Component Analysis on PBMC data generated with live and heat treated (140° C., 15") probiotic and dairy starter strains revealed that live strains are spread all along the x axis, illustrating that strains exhibit very different immune profiles in vitro, from low (left side) to high (right side) inducers of pro-inflammatory cytokines. Heat treated strains cluster on the left side of the graph, showing that pro-inflammatory cytokines are much less induced by heat treated strains (FIG. 6). By contrast, bacteria heat treated at 85° C. for 20 min induced more pro-inflammatory cytokines and less IL-10 than live cells resulting in higher IL-12p40/IL-10 ratios (FIG. 7).

Anti-inflammatory profiles are enhanced or generated by UHT-like and HTST-like treatments.

Figure 1A:
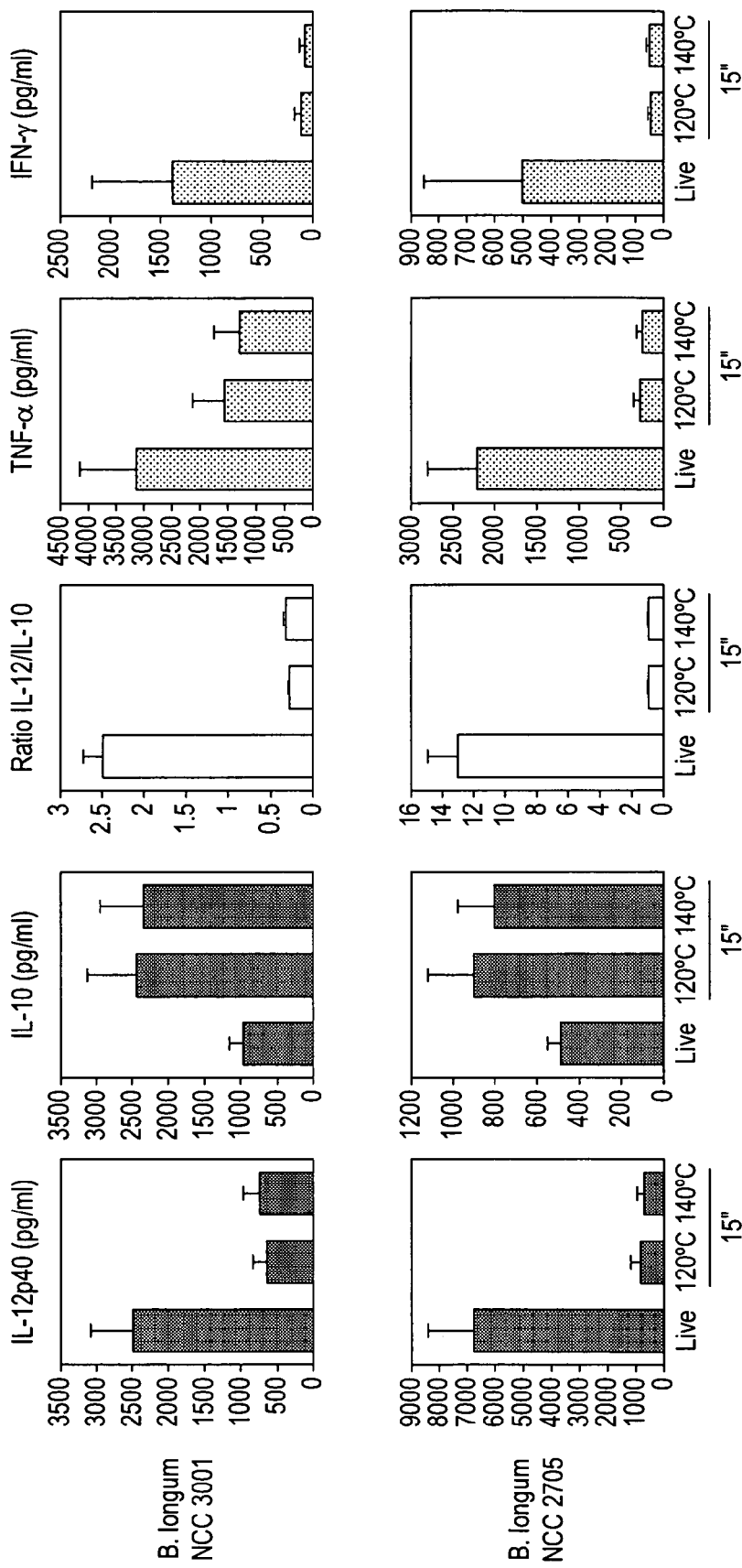
Figure 1B:
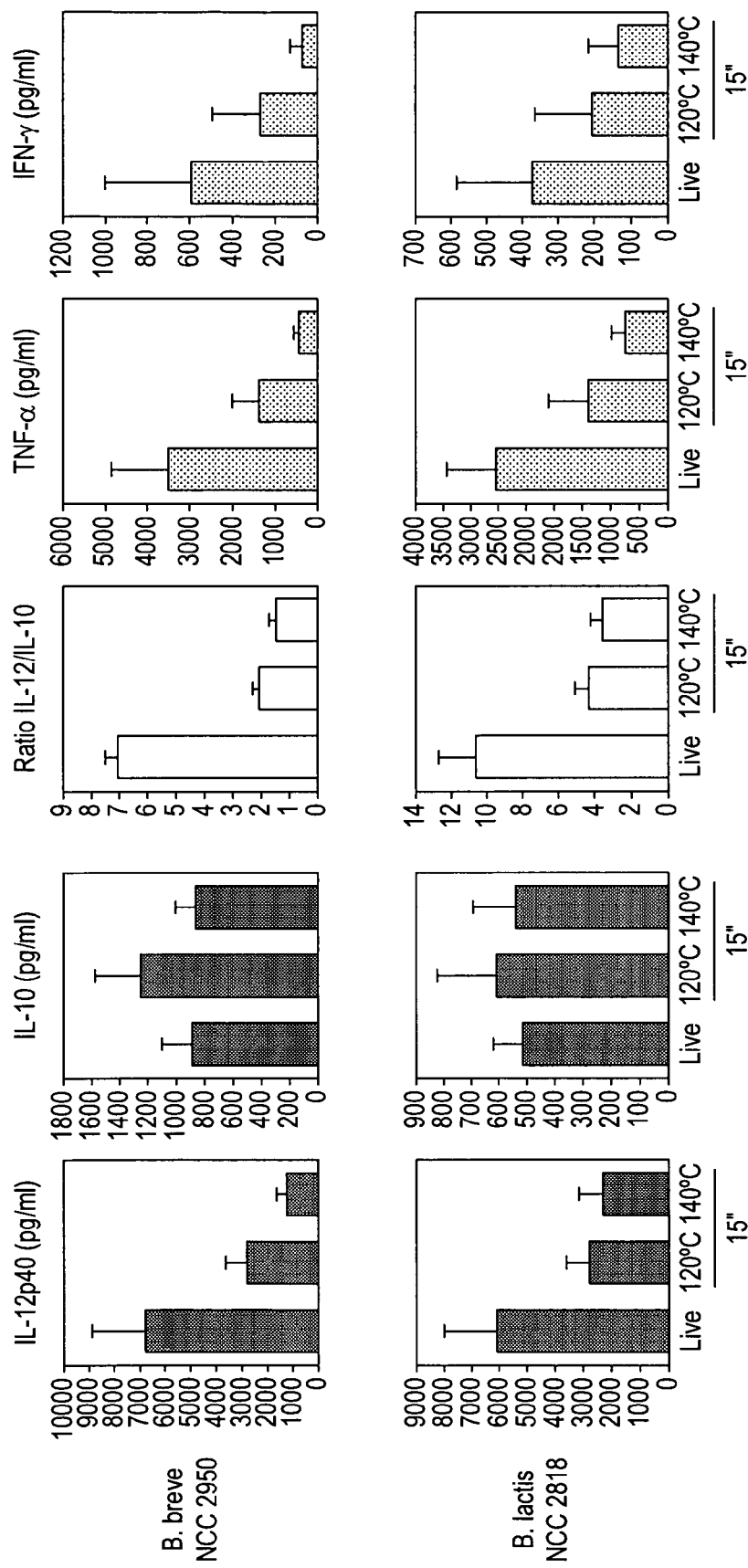
Figure 2:
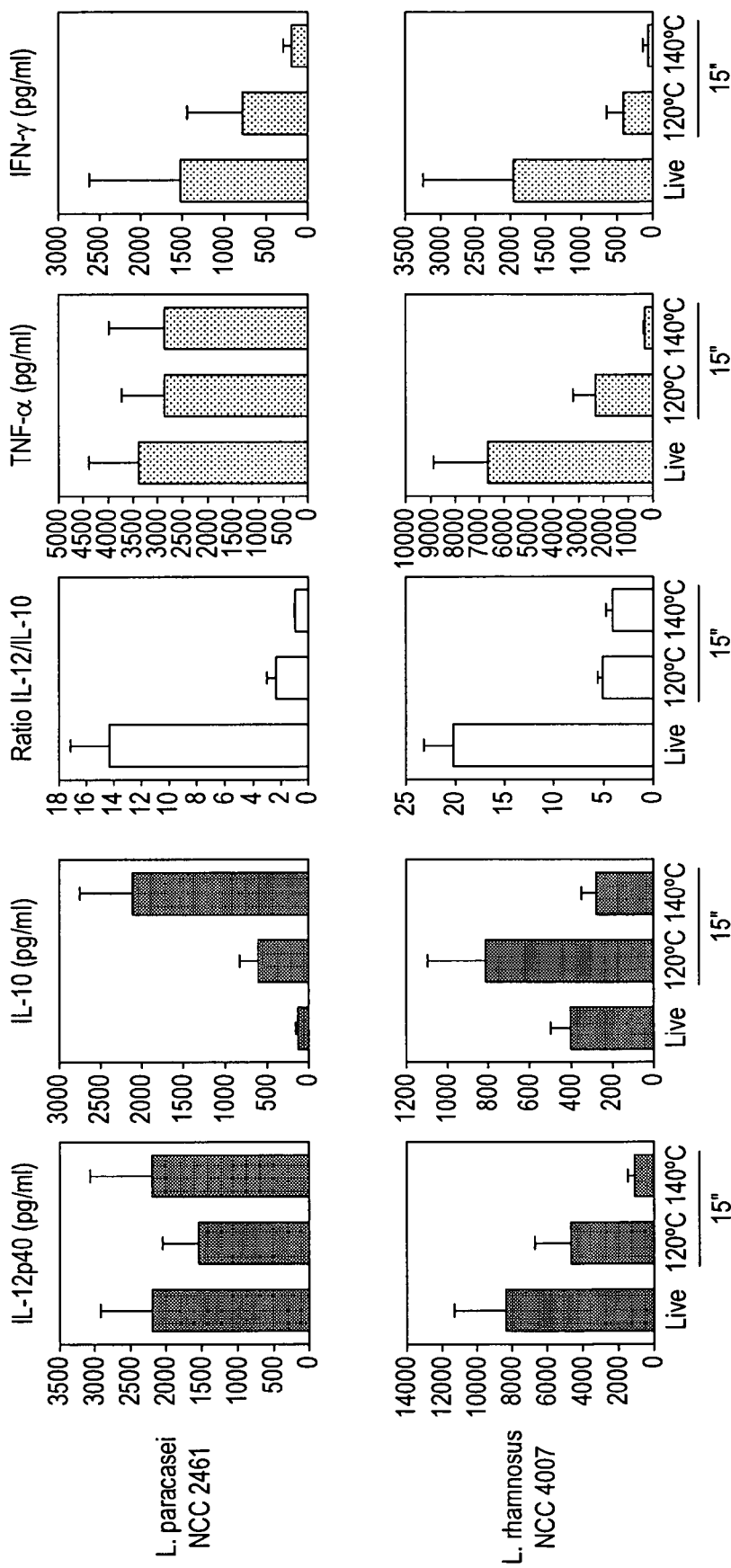
Figure 3A:
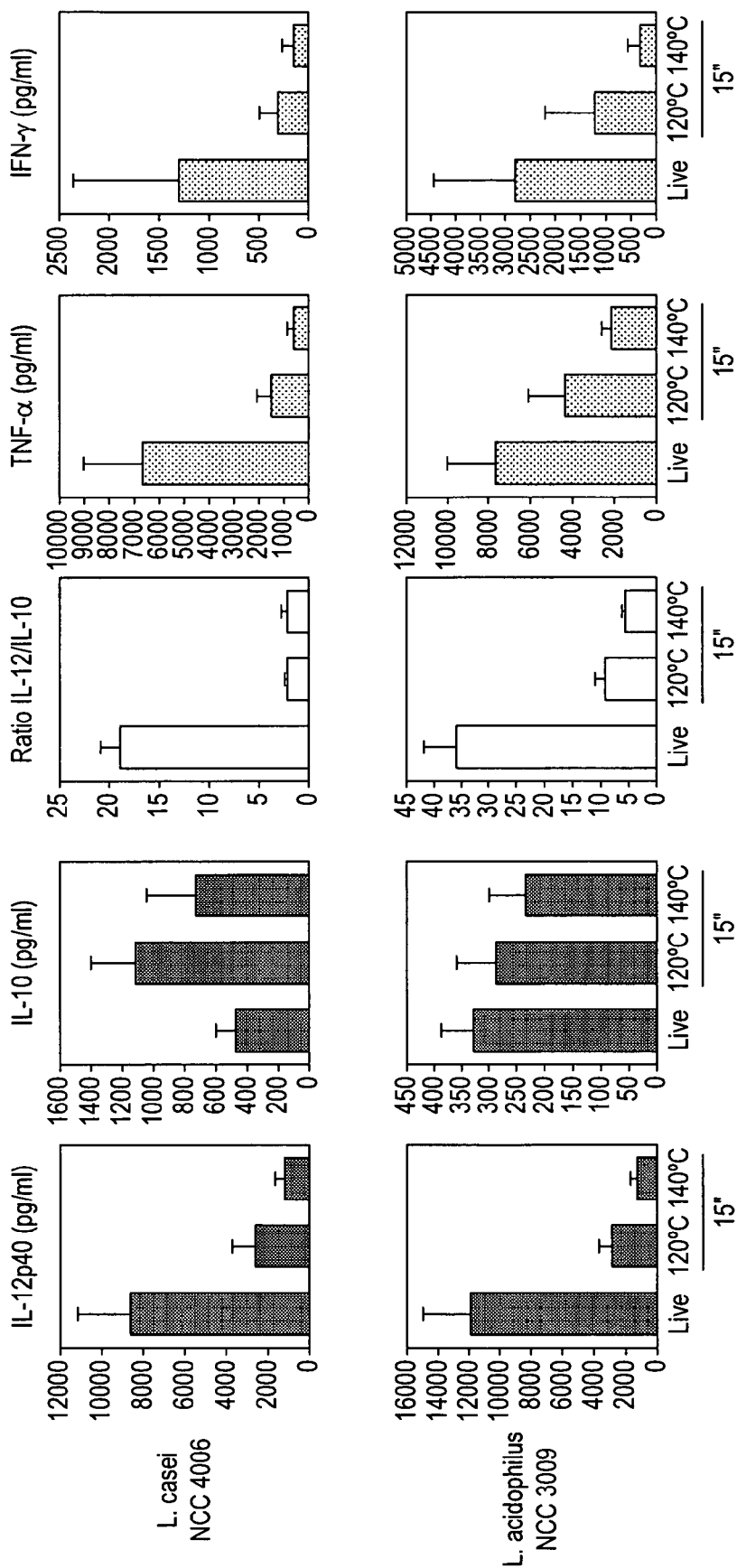
Figure 3B:
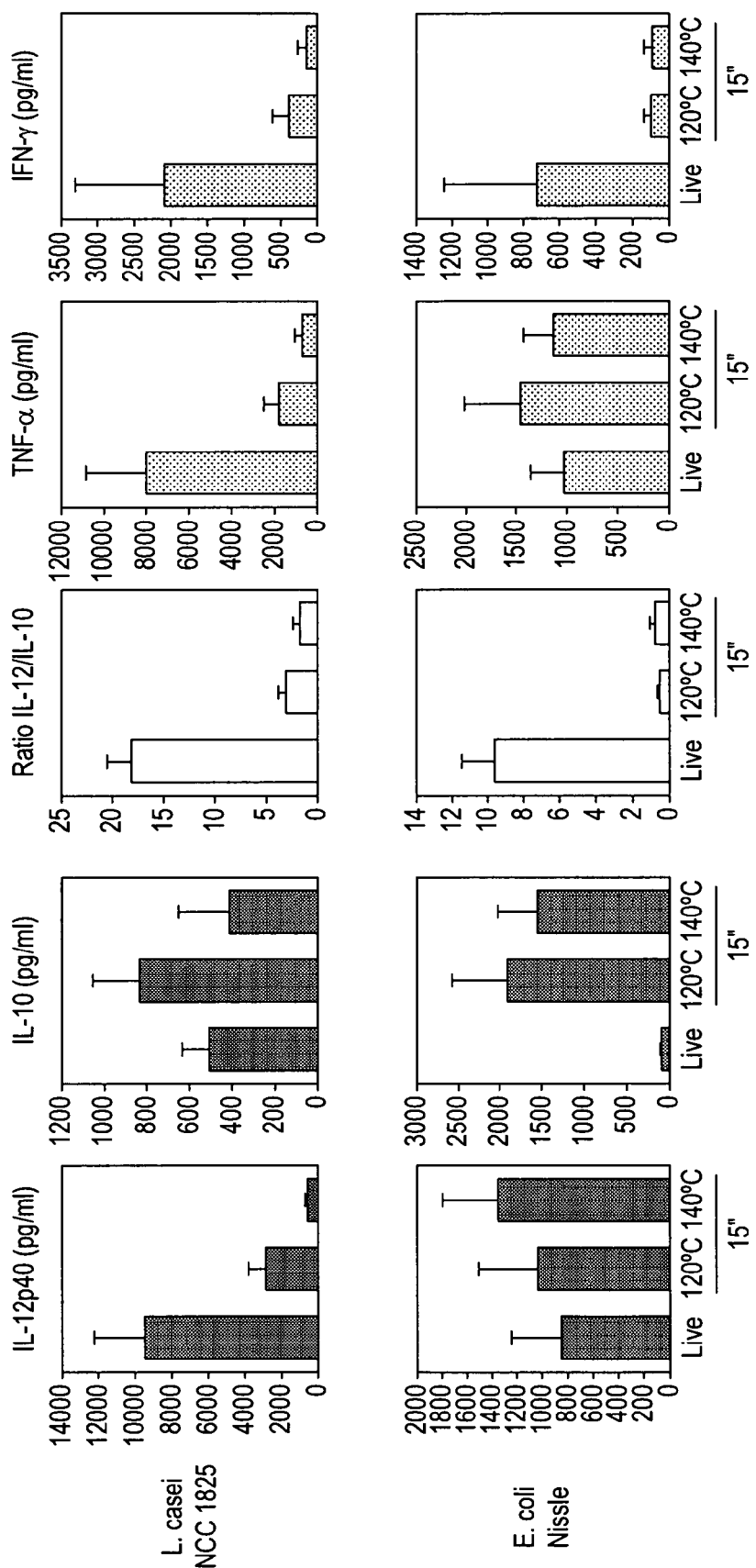

UHT and HTST treated strains exhibit anti-inflammatory profiles regardless of their respective initial immune profiles (live cells). Probiotic strains known to be anti-inflammatory in vivo and exhibiting anti-inflammatory profiles in vitro (*B. longum* NCC 3001, *B. longum* NCC 2705, *B. breve* NCC 2950, *B. lactis* NCC 2818) were shown to exhibit enhanced anti-inflammatory profiles in vitro after "short-time high temperature" treatments. As shown in FIG. 1, the IL-12p40/IL-10 ratios of UHT-like treated *Bifidobacterium* strains were lower than those from the live counterparts, thus showing improved anti-inflammatory profiles of UHT-like treated samples. More strikingly, the generation of anti-inflammatory profiles by UHT-like and HTST-like treatments was also confirmed for non anti-inflammatory live strains. Both live *L. rhamnosus* NCC 4007 and *L. paracasei* NCC 2461 exhibit high IL-12p40/IL-10 ratios in vitro (FIGS. 2 and 5). The two live strains were shown to be not protective against TNBS-induced colitis in mice. The IL-12p40/IL-10 ratios induced by *L. rhamnosus* NCC 4007 and *L. paracasei* NCC 2461 were dramatically reduced after "short-time high temperature" treatments (UHT or HTST) reaching levels as low as those obtained with *Bifidobacterium* strains. These low IL-12p40/IL-10 ratios are due to low levels of IL-12p40 production combined with no change (*L. rhamnosus* NCC 4007) or a dramatic induction of IL-10 secretion (*L. paracasei* NCC 2461) (FIG. 2).

As a Consequence:

Anti-inflammatory profiles of live micro-organisms can be enhanced by UHT-like and HTST-like heat treatments (for instance *B. longum* NCC 2705, *B. longum* NCC 3001, *B. breve* NCC 2950, *B. lactis* NCC 2818)

Anti-inflammatory profiles can be generated from non anti-inflammatory live micro-organisms (for example *L. rhamnosus* NCC 4007, *L. paracasei* NCC 2461, dairy starters *S. thermophilus* NCC 2019) by UHT-like and HTST-like heat treatments.

Anti-inflammatory profiles were also demonstrated for strains isolated from commercially available products (FIGS. 3 A & B) including a probiotic *E. coli* strain.

The impact of UHT/HTST-like treatments was similar for all tested probiotics and dairy starters, for example lactobacilli, bifidobacteria and streptococci.

UHT/HTST-like treatments were applied to several lactobacilli, bifidobacteria and streptococci exhibiting different in vitro immune profiles. All the strains induced less pro-inflammatory cytokines after UHT/HTST-like treatments than their live counterparts (FIGS. 1, 2, 3, 4, 5 and 6) demonstrating that the effect of UHT/HTST-like treatments on the immune properties of the resulting non replicating bacteria can be generalized to all probiotics, in particular to lactobacilli and bifidobacteria and specific *E. coli* strains and to all dairy starter cultures in particular to streptococci, lactococci and lactobacilli.

EXAMPLE 2

Methodology

Bacterial Preparations:

Five probiotic strains were used to investigate the immune boosting properties of non-replicating probiotics: 3 bifidobacteria (*B. longum* NCC3001, *B. lactis* NCC2818, *B. breve* NCC2950) and 2 lactobacilli (*L. paracasei* NCC2461, *L. rhamnosus* NCC4007).

Bacterial cells were grown on MRS in batch fermentation at 37° C. for 16-18 h without pH control. Bacterial cells were spun down (5,000×g, 4° C.) and resuspended in phosphate buffer saline prior to be diluted in saline water in order to reach a final concentration of around 10E10 cfu/ml. *B. longum* NCC3001, *B. lactis* NCC2818, *L. paracasei* NCC2461, *L. rhamnosus* NCC4007 were heat treated at 85° C. for 20 min in a water bath. *B. breve* NCC2950 was heat treated at 90° C. for 30 minutes in a water bath. Heat treated bacterial suspensions were aliquoted and kept frozen at −80° C. until use. Live bacteria were stored at −80° C. in PBS-glycerol 15% until use.

In Vitro Immunoprofiling of Bacterial Preparations

The immune profiles of live and heat treated bacterial preparations (i.e. the capacity to induce secretion of specific cytokines from human blood cells in vitro) were assessed. Human peripheral blood mononuclear cells (PBMCs) were isolated from blood filters. After separation by cell density gradient, mononuclear cells were collected and washed twice with Hank's balanced salt solution. Cells were then resuspended in Iscove's Modified Dulbecco's Medium (IMDM, Sigma) supplemented with 10% foetal calf serum (Bioconcept, Paris, France), 1% L-glutamine (Sigma), 1% penicillin/ streptomycin (Sigma) and 0.1% gentamycin (Sigma). PBMCs ($7 \times 10^5$ cells/well) were then incubated with live and heat treated bacteria (equivalent $7 \times 10^6$ cfu/well) in 48 well plates for 36 h. The effects of live and heat treated bacteria were tested on PBMCs from 8 individual donors splitted into two separate experiments. After 36 h incubation, culture plates were frozen and kept at −20° C. until cytokine measurement. Cytokine profiling was performed in parallel (i.e. in the same experiment on the same batch of PBMCs) for live bacteria and their heat-treated counterparts.

Levels of cytokines (IFN-γ, IL-12p40, TNF-α and IL-10) in cell culture supernatants after 36 h incubation were determined by ELISA (R&D DuoSet Human IL-10, BD OptEIA Human IL12p40, BD OptEIA Human TNF, BD OptEIA Human IFN-γ) following manufacturer's instructions. IFN-γ, IL-12p40 and TNF-α are pro-inflammatory cytokines, whereas IL-10 is a potent anti-inflammatory mediator. Results are expressed as means (pg/ml) +/− SEM of 4 individual donors and are representative of two individual experiments performed with 4 donors each.

In Vivo Effect of Live and Heat Treated *Bifidobacterium Breve* NCC2950 in Prevention of Allergic Diarrhea A mouse model of allergic diarrhea was used to test the Th1 promoting effect of *B. breve* NCC2950 (Brandt E. B et al. JCI 2003; 112(11): 1666-1667). Following sensitization (2 intraperitoneal injections of Ovalbumin (OVA) and aluminium potassium sulphate at an interval of 14 days; days 0 and 14) male Balb/c mice were orally challenged with OVA for 6 times (days 27, 29, 32, 34, 36, 39) resulting in transient clinical symptoms (diarrhea) and changes of immune parameters (plasma concentration of total IgE, OVA specific IgE, mouse mast cell protease 1, i.e MMCP-1). *Bifidobacterium breve* NCC2950 live or heat treated at 90° C. for 30 min, was administered by gavage 4 days prior to OVA sensitization (days −3, −2, −1, 0 and days 11, 12, 13 and 14) and during the challenge period (days 23 to 39). A daily bacterial dose of around $10^9$ colony forming units (cfu) or equivalent cfu/mouse was used.

Results

Induction of Secretion of 'Pro-Inflammatory' Cytokines After Heat Treatment

The ability of heat treated bacterial strains to stimulate cytokine secretion by human peripheral blood mononuclear cells (PBMCs) was assessed in vitro. The immune profiles based on four cytokines upon stimulation of PBMCs by heat treated bacteria were compared to that induced by live bacterial cells in the same in vitro assay.

The heat treated preparations were plated and assessed for the absence of any viable counts. Heat treated bacterial preparations did not produce colonies after plating.

Figure 8:
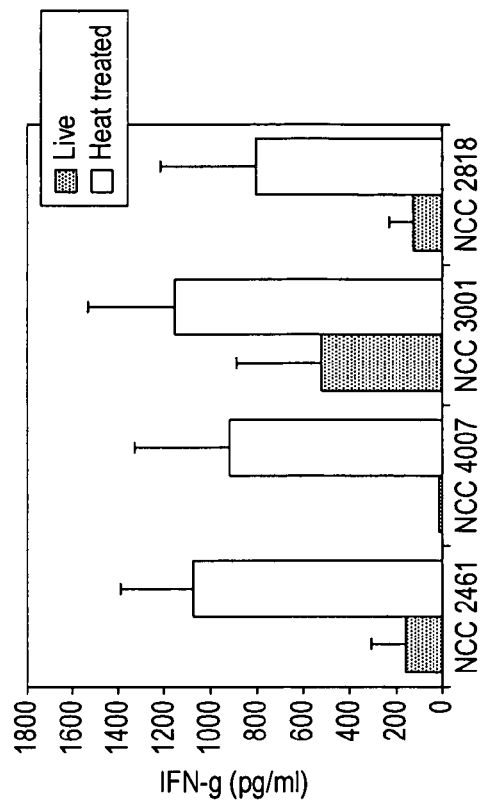
FIG. 8 shows the enhancement of in vitro cytokine secretion from human PBMCs stimulated with heat treated bacteria.
Figure 8:
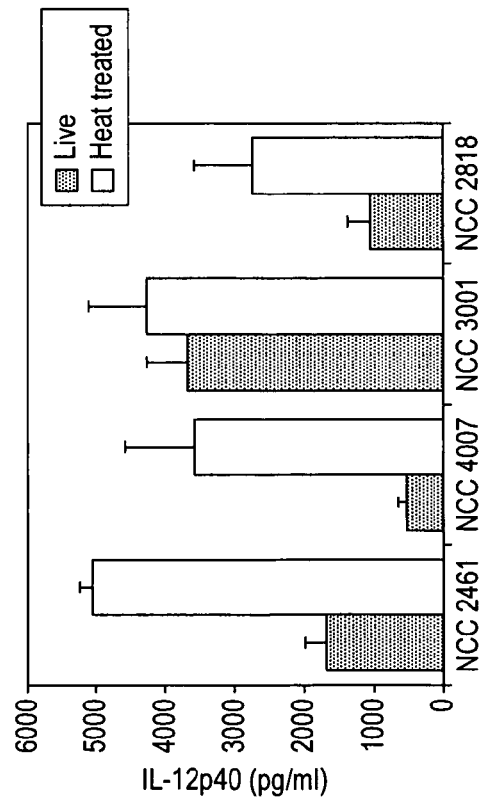
Figure 8:
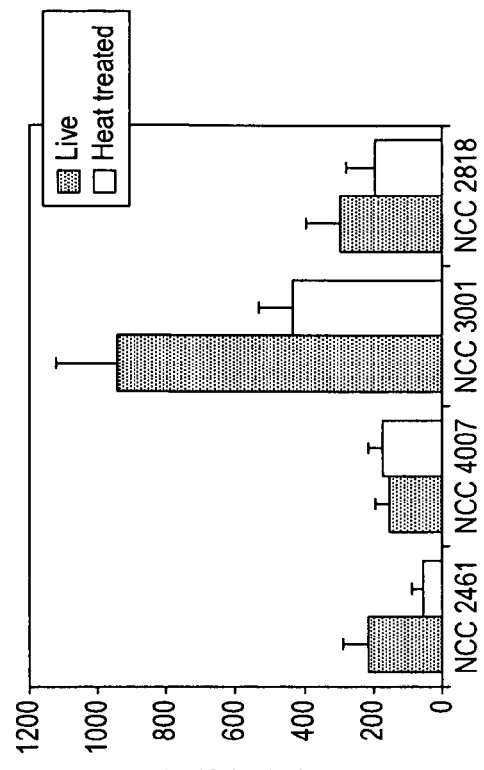
Figure 8:
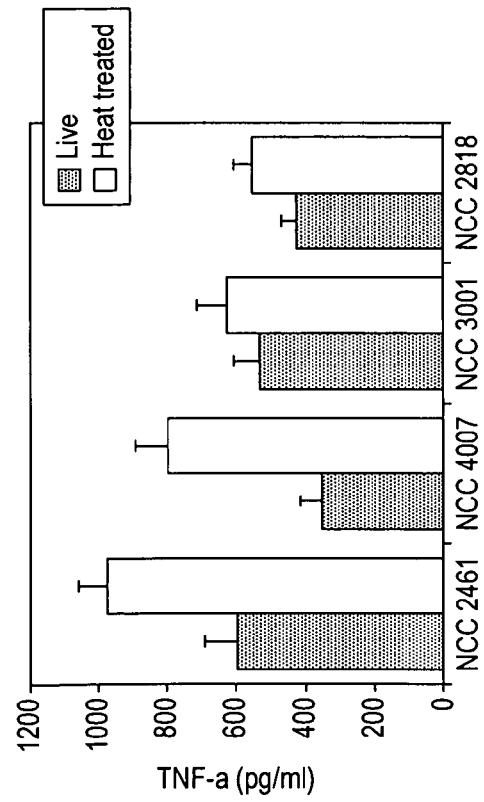

Live probiotics induced different and strain dependent levels of cytokine production when incubated with human PBMCs (FIG. 8). Heat treatment of probiotics modified the levels of cytokines produced by PBMCs as compared to their live counterparts. Heat treated bacteria induced more pro-inflammatory cytokines (TNF-α, IFN-γ, IL-12p40) than their live counterparts do. By contrast heat treated bacteria induced similar or lower amounts of IL-10 compared to live cells (FIG. 8). These data show that heat treated bacteria are more able to stimulate the immune system than their live counterparts and therefore are more able to boost weakened immune defences. In other words the in vitro data illustrate an enhanced immune boost effect of bacterial strains after heat treatment.

In order to illustrate the enhanced effect of heat-treated *B. breve* NCC2950 (compared to live cells) on the immune system, both live and heat treated *B. breve* NCC2950 (strain A) were tested in an animal model of allergic diarrhea.

As compared to the positive control group, the intensity of diarrhea was significantly and consistently decreased after treatment with heat treated *B. breve* NCC2950 (41.1%±4.8) whereas the intensity of diarrhea was lowered by only 20±28.3% after treatment with live *B. breve* NCC2950. These results demonstrate that heat-treated *B. breve* NCC2950 exhibits an enhanced protective effect against allergic diarrhea than its live counterpart (FIG. 9).

As a consequence, the ability of probiotics to enhance the immune defences was shown to be improved after heat treatment.

EXAMPLES 3-6

The following nutritional compositions may be prepared, for example

|  | Formulation A | Formulation B | Formulation C | Formulation D |
|---|---|---|---|---|
| kcal/mL | 1.0 | 1.0 | 1.0 | 1.0 |
| Caloric Distribution (% of kcal) | Protein 12% Carbohydrate 44% Fat 44% | Protein 12% Carbohydrate 44% Fat 44% | Protein 12% Carbohydrate 55% Fat 33% | Protein 12% Carbohydrate 55% Fat 33% |
| Protein Source | milk protein concentrate, whey protein concentrate | milk protein concentrate, whey protein concentrate | enzymatically hydrolyzed whey protein | enzymatically hydrolyzed whey protein |
| NPC:N Ratio | 183:1 | 183:1 | 183:1 | 183:1 |
| MCT:LCT Ratio | 21:79 | 21:79 | 60:40 | 60:40 |
| n6:n3 Ratio | 5.3:1 | 5.3:1 | 4.8:1 | 4.8:1 |
| Osmolality (mOsm/kg water) | 350 | 350 | 260-380 | 390 |
| Free Water | 85% | 85% | 85% | 85% |
| Renal Solute Load (mOsm/L) | 265 | 265 | 255 | 255 |

-continued

|  | Formulation A | Formulation B | Formulation C | Formulation D |
|---|---|---|---|---|
| Fiber Content |  | 6 g/L (pea fiber, oligofructose, inulin) |  | 7.2 g/L (pea fiber, oligofructose, inulin) |
| Probiotics | $10^9$ cfu *Lactobacillus johnsonii* La1 | $10^9$ cfu heat treated (75° C., 20 min) *Bifidobacterium longum* NCC 3001 | $10^9$ cfu UHT treated *Lactobacillus johnsonii* La1 | $10^9$ cfu UHT treated *Bifidobacterium breve* NCC 2950 |

The invention claimed is:

1. A method for providing complete nutrition to a child suffering from an impaired gastro-intestinal tract function comprising administering a composition comprising probiotic *Bifidobacterium breve* NCC 2950 micro-organisms to the child, and the probiotic *Bifidobacterium breve* NCC 2950 micro-organisms have been heat treated at a temperature of 120-140° C. for 1-120 seconds.

2. The method in accordance with claim 1, wherein the composition has a caloric density of 0.9-1.1 kcal/ml, an osmolality of 250-270 mOsm/kg water, and comprising a protein source comprising 11-13% of the calories of the composition, a carbohydrate source comprising 43-56% of the calories of the composition, a lipid source comprising 32-45% of the calories of the composition, and having a non-protein calorie to nitrogen ratio (NPC:N) in the range of 175:1 to 190:1.

3. The method in accordance with claim 1, wherein the composition comprises a lipid source with a n6:n3 fatty acid ratio in the range of 4.5:1 to 5.5:1.

4. The method in accordance with claim 1, wherein the composition comprises 83-87% free water.

5. The method in accordance with claim 1, wherein the probiotic *Bifidobacterium breve* NCC 2950 micro-organisms comprise non-replicating probiotic *Bifidobacterium breve* NCC 2950 micro-organisms.

6. The method in accordance with claim 1, comprising probiotic micro-organisms in an amount corresponding to $10^6$ to $10^{12}$ cfu.

7. The method in accordance with claim 1, wherein at least 90% of the probiotics are non-replicating.

8. The method in accordance with claim 1, wherein the composition comprises 0.005 mg-1000 mg non-replicating micro-organisms per daily dose.

9. The method in accordance with claim 1, wherein the composition comprises a lipid source comprising medium chain triglycerides (MCT) and long chain triglycerides (LCT) with an MCT:LCT ratio in the range of 20:80 to 62:38.

* * * * *